United States Patent [19]
Svoboda et al.

[11] Patent Number: 5,661,245
[45] Date of Patent: Aug. 26, 1997

[54] FORCE SENSOR ASSEMBLY WITH INTEGRATED RIGID, MOVABLE INTERFACE FOR TRANSFERRING FORCE TO A RESPONSIVE MEDIUM

[75] Inventors: Eugene V. Svoboda, Saratoga; James T. Cook, Sr., Antioch; Christos D. Cartsonas, Menlo Park, all of Calif.

[73] Assignee: SenSym, Incorporated, Milpitas, Calif.

[21] Appl. No.: 501,821

[22] Filed: Jul. 14, 1995

[51] Int. Cl.$^6$ ............................. G01L 9/04; G01L 1/02; G01L 5/08

[52] U.S. Cl. ........................... 73/726; 73/862.581

[58] Field of Search .......................... 73/720, 721, 726, 73/756, 862, 581

[56] References Cited

U.S. PATENT DOCUMENTS

| | | | |
|---|---|---|---|
| 2,488,347 | 11/1949 | Thurston | 73/726 |
| 3,439,541 | 4/1969 | Gilder | 73/726 |
| 5,209,121 | 5/1993 | Haefner | 73/727 |
| 5,218,972 | 6/1993 | Gorsuch et al. | 73/727 |
| 5,392,653 | 2/1995 | Zanger et al. | 73/726 |
| 5,438,877 | 8/1995 | Vowles et al. | 73/756 |

FOREIGN PATENT DOCUMENTS 759876  8/1980  U.S.S.R. .................... 73/726

Primary Examiner—George M. Dombroske
Assistant Examiner—William L. Oen
Attorney, Agent, or Firm—Skjerven, Morrill, MacPherson, Franklin & Friel; Kent B. Chambers; Norman R. Klivans

[57] ABSTRACT

A force sensor assembly incorporates an integrated plunger to provide an economical assembly which can be calibrated and mounted as a single unit. The force sensor assembly utilizes a retainer to movably capture a solid interface within an opening in the retainer. The solid interface includes a flange positioned within the assembly below the retainer opening. The flange dimensions are greater than the retainer opening to retain the solid interface within the assembly. The retainer is attached to a housing body having a gel filled cavity underlying the retainer opening. A diaphragm free floats on the gel within the housing body and contacts the solid interface. The gel transmits a force exerted on the diaphragm from the solid interface to a pressure sensor mounted at the base of the housing body cavity. A ceramic substrate having an integrated resistor network supports the pressure sensor and an amplifier. The pressure sensor and accompanying electronic components provide a conditioned electrical signal corresponding to the force applied to the solid interface.

33 Claims, 4 Drawing Sheets

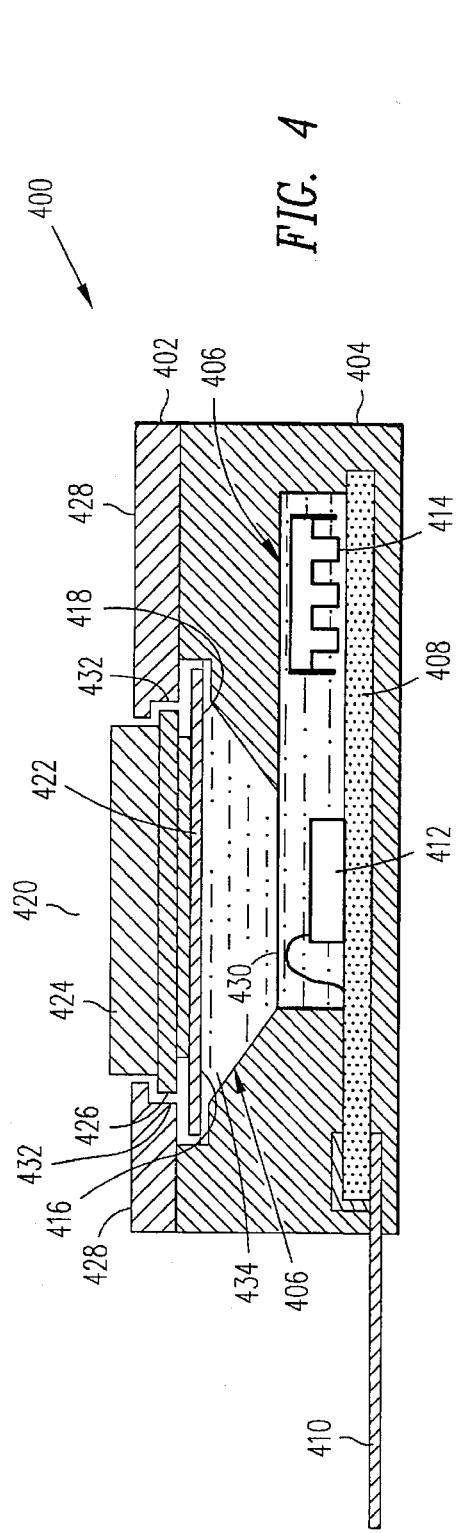
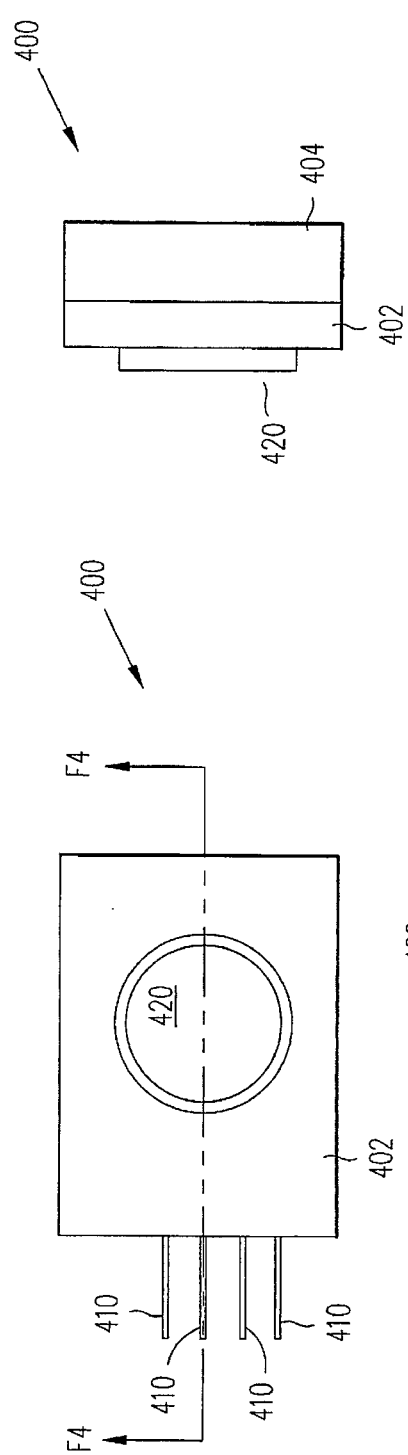
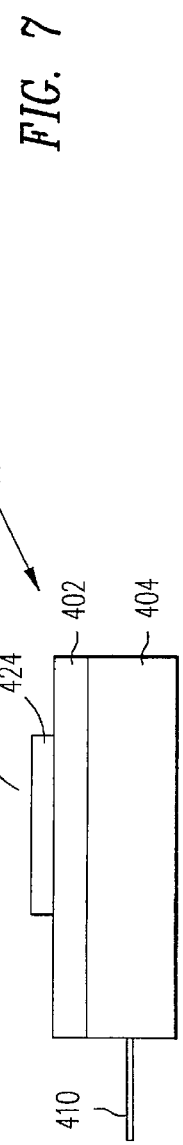
FIG. 4
FIG. 5
FIG. 6
FIG. 7

1

FORCE SENSOR ASSEMBLY WITH INTEGRATED RIGID, MOVABLE INTERFACE FOR TRANSFERRING FORCE TO A RESPONSIVE MEDIUM

FIELD OF THE INVENTION

This invention relates to force sensor assemblies and more particularly relates to force sensor assemblies for measuring pressure in flexible tubing.

BACKGROUND

The acquisition of force data, often in the form of pressure measurement, is important for numerous applications. The automotive and medical industries utilize force sensor and pressure measuring systems to, for example, monitor and control a variety of substances and equipment. For example, in the medical industry precise and accurate information regarding the infusion into a patient of intravenous ("I.V.") solutions through I.V. tubing and of nutrients through tubing and a feeding pump can be critical to the patient's well being.

To properly control and monitor the infusion flow rate of I.V. solutions, force sensors may be positioned to measure the I.V. solution pressure. FIG. 1, labeled prior art, illustrates in cross-section an I.V. tube 102 compressively engaged between a solid surface 104 and a force sensor 106. One approach to measuring I.V. solution pressure within tube 102 involves capturing and partially compressing I.V. tube 102 between force sensor 106 and solid surface 104. The force sensor 106 detects a force on the tubal wall 108 corresponding to varying I.V. solution pressure exerted within tube 102. A force sensor output signal corresponding to the I.V. solution pressure may be used to calculate, for example, I.V. solution flow rates or check for occlusions in the I.V. solution flow path. A variety of well known distribution systems, such as peristaltic pumps and syringe pumps, utilize force sensor acquired information to control and monitor the infusion of I.V. solutions. However, when used in pressure measuring applications, force sensor 106 is generally expensive and/or suffers from long term stability problems.

FIG. 2, labeled prior art, illustrates in a plan view another conventional approach ("bladder approach") to measuring I.V. solution pressure involving a bladder housing 200 ("bladder approach") having flexible bladder 212 placed in series with I.V. tubes 204 and 208. In the bladder approach, bladder housing end 202 connects to an I.V. tube 204 which is connected to a solution source (not shown), and bladder housing end 206 connects to an I.V. tube 208 which is connected to a solution destination (not shown). The bladder housing 200 includes flexible pumping bladders 210 and 214. Bladders 210, 212, and 214 fill with I.V. solution as I.V. solution is pumped through the bladder housing 200.

Referring to FIG. 3, labeled prior art, in cross-section bladder housing 200 is illustrated having end regions positioned between solid surface 302, which is part of a pump housing, and pressure sensor 304. During operation, I.V. solution fills the interior of bladder housing 200, and pump piston 312 impinges upon bladder 212. Bladder 212, containing I.V. solution 314, transfers the pressure of the I.V. solution 314 to pressure sensor 304 through flexible bladder underside 316, protective membrane 308, and gel 310. Pressure sensor 304 typically employs a piezoresistive silicon pressure sensor 306 which provides high reliability at a low cost. However, to ensure sterility of the I.V. solution

2 transported through bladder housing 200, the tubing 204 and 208 and bladder housing 200 must be disposable and periodically replaced which increases the operating cost of the bladder approach. Additionally, the bladder approach requires a bladder housing 200 separate from the force sensor.

SUMMARY

The present invention is directed to an economical force sensor assembly and a coupled solid interface that, in one embodiment, senses solution pressure in solutions transmitted via tubing. When used with a tubal solution distribution system, in another embodiment, the force sensor assembly includes a pressure sensor housing having an integral solid interface for direct tubal impingement which avoids direct contact with tubal solution.

In another embodiment the force sensor assembly pressure sensor housing utilizes a retainer having an opening to movably capture an integral solid interface structure. In this embodiment, the solid interface includes a flange positioned within the assembly below the retainer opening, and the flange dimensions are greater than the retainer opening to capture the solid interface structure within the assembly. The retainer is attached to the pressure sensor housing and separated from a gel-filled cavity underlying the retainer opening within the pressure sensor housing by a diaphragm on the gel. Furthermore, in this embodiment following force application to the solid interface structure, the gel transmits the force exerted on the diaphragm from the solid interface structure to a pressure sensor mounted at the base of the housing body cavity. In another embodiment, a ceramic substrate having an integrated resistor network supports the pressure sensor and an amplifier, and the pressure sensor and accompanying electronic components provide a conditioned electrical signal corresponding to the force applied to the solid interface structure.

In another embodiment a force sensor assembly has a housing that includes a retainer and a cavity, the retainer having an opening in communication with the cavity. The force sensor assembly further includes a pressure sensor at least partially disposed within the housing, a solid interface movably captured by the retainer and having a portion extending through the retainer opening away from the housing, and a pressure transmitter disposed within the cavity and in contact with the pressure sensor and the solid interface.

BRIEF DESCRIPTION OF THE DRAWINGS

Reference numerals referring to the same feature appearing in multiple figures are the same.

FIG. 4 illustrates a cross-sectional side view of a force sensor assembly with integrated plunger in accordance with the invention.

FIG. 5 illustrates a top view of the force sensor assembly of FIG. 4.

FIG. 6 illustrates a side view of the force sensor assembly of FIG. 4.

FIG. 7 illustrates a front view of the force sensor assembly of FIG. 4.

DETAILED DESCRIPTION

Figure 1:
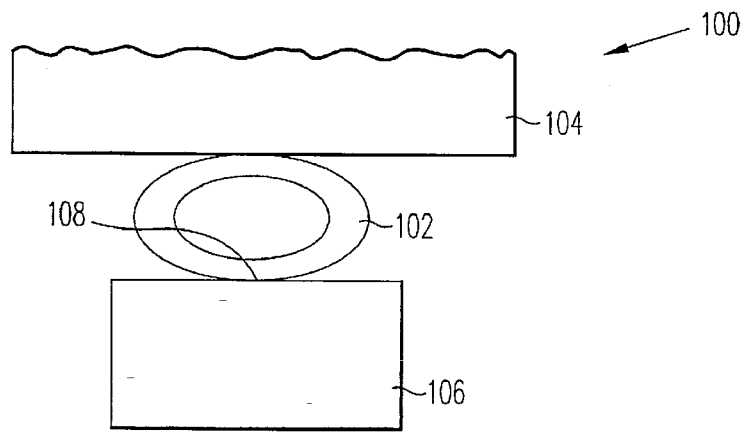
FIG. 1, labeled prior art, illustrates tubing compressed between a solid surface and a force sensor.
Figure 2:
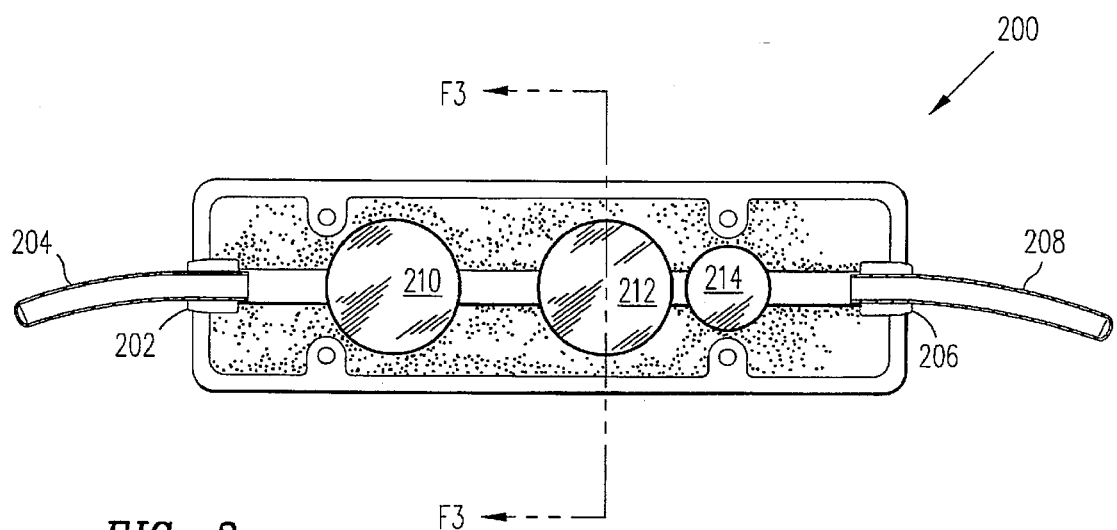
FIG. 2, labeled prior art, illustrates a bladder housing and connected tubing.
Figure 3:
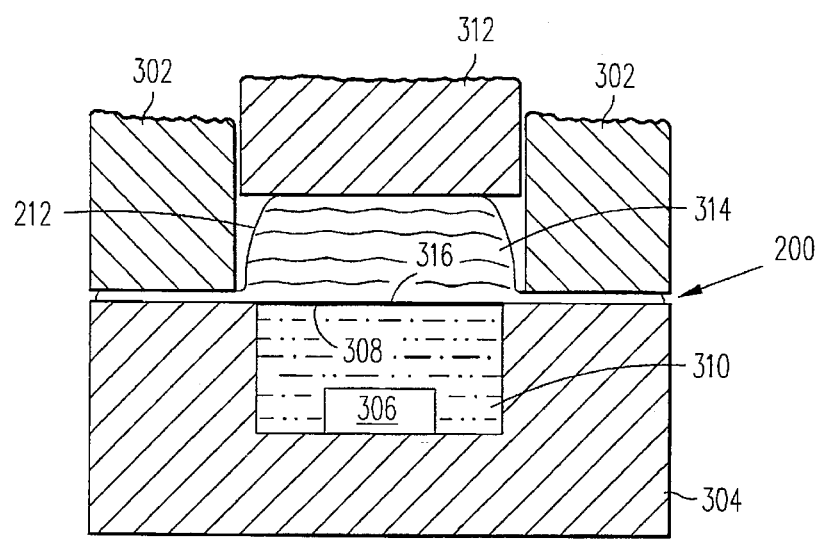
FIG. 3, labeled prior art, illustrates the bladder housing situated between a solid surface and a pressure sensor.

The following description is intended to be illustrative only and not limiting.

FIG. 4 illustrates a cross-sectional side view of a force sensor assembly 400 in one embodiment of the invention. The force sensor assembly housing consists primarily of injection molded Ultem® plastic interface retainer 402 and injection molded Ultem® housing body 404. Ultem® is manufactured by G. E. Plastics, a Mount Vernon, Indiana company. The housing body 404 includes a gel and electronic component cavity 406.

Cavity 406 has a 0.59 inch (15 mm) thick by 0.025 inch (0.64 mm) diameter cylindrical portion surrounding diaphragm 418. The diameter of cavity 406 decreases to 0.445 inches (11.3 mm) and tapers to a 0.25×0.21 inch (6.35×5.33 mm) rectangular opening 430. The tapered portion 434 of cavity 406 terminates with a 0.325×0.250×0.040 inch (8.26× 6.35×1.02 mm) cavity portion.

Ceramic substrate 408, for example, an alumina ($Al_2O_3$ 96%) substrate, is recessed into plastic housing body 404 and attached with an epoxy adhesive. The ceramic substrate 408 provides a boundary for cavity 406. The exposed underside of substrate 408 beneficially allows laser trimming of an included conventional integrated trimmable resistor network (not shown) as needed to calibrate force sensor assembly 400. The substrate 408 may be fabricated from a variety of ceramic and non-ceramic materials preferably having thermal expansion coefficients compatible with housing body 404. Metallic leads 410, through thick film metal connections, electrically couple force sensor assembly 400 to external conventional electrical systems (not shown) such as a peristaltic pump or a syringe pump control system.

Prior to attaching ceramic substrate 408 to housing body 404, micro-machined pressure sensor 412 e.g. part no. P382A035SG from SenSym Inc., a Milpitas, Calif. company, and integrated circuit amplifier 414 e.g., part no. LM324 from National Semiconductor Corp., a California company, are conventionally mounted and electrically connected to ceramic substrate 408. Ceramic substrate 408, pressure sensor 412, and amplifier 414 form a well-known hybrid circuit for sensing pressure and providing a conditioned, calibrated output representing sensed pressure.

Figure 12:
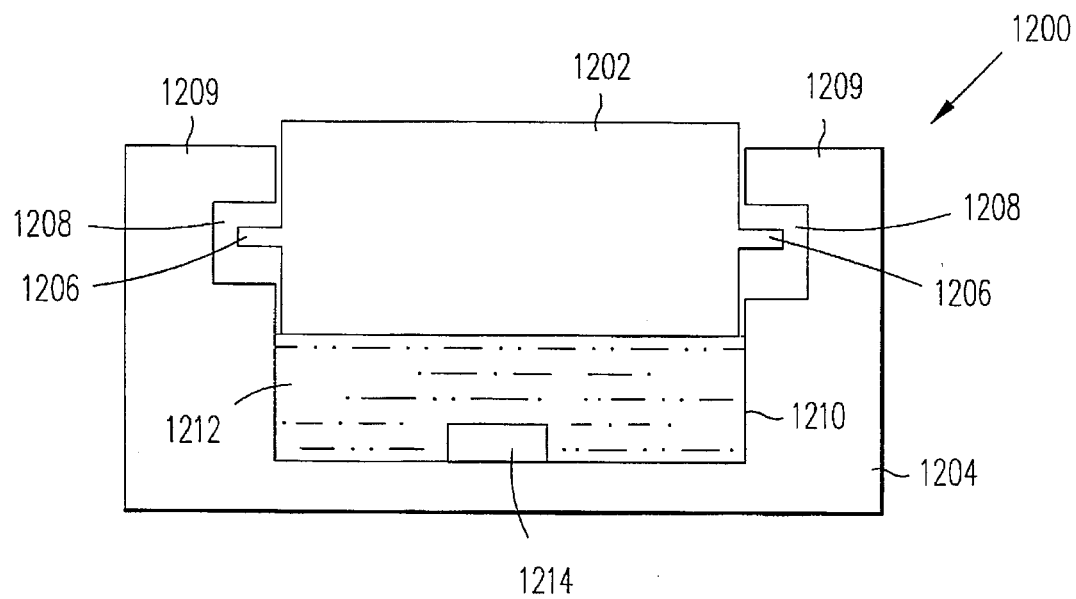
FIG. 12 illustrates a cross-sectional view of a force sensor assembly having a plunger within a housing directly impinging on a gel.

Cavity 406 is preferably filled with a gel 416, for example, silicone based gel such as deformable Sylgard 527 manufactured by Dow Corning Corp., a Midland, Mich. company. The 0.13 inch (0.330 mm) thick by 0.570 inch (14.5 mm) diameter interface diaphragm 418 is preferably an elastomer, for example, a fabric reinforced Viton® membrane having a thickness of 0.13 inches (0.33 mm), that free floats on the surface of gel 416. Although diaphragm 418 may free float to accommodate thermal expansion of gel 416, diaphragm 418 may be fastened to housing body 404 using, for example, clamps. Although the diameter of diaphragm 418 is less than the surrounding cavity 406 diameter, the viscosity of gel 416 forecloses leakage. Additionally, although force sensor assembly 400 interposes diaphragm 418 between gel 416 and plunger 420, plunger 420 may directly contact gel 416 by providing for example, a non-leaking seal between plunger 420 and retainer 402 or a close tolerance between plunger 420 and cavity 406 (FIG. 12).

Injection molded, Ultem® plastic plunger 420 preferably rests on diaphragm 418 but may alternatively be attached to diaphragm 418. Plunger 420 includes a 0.020 inch (0.508 mm) thick by 0.365 inch (9.27 mm) diameter cylindrical diaphragm engagement portion 422, a 0.050 inch (1.27 mm) thick by 0.37 inch (9.4 mm) diameter cylindrical external interface portion 424, and a 0.017 inch (0.432 mm) thick by 0.485 inch (12.3 mm) diameter cylindrical flange portion 426 interposed between diaphragm portions 422 and 424.

Retainer 402 is fastened to body 404 preferably after filling cavity 406 with gel 416, placing diaphragm 418 on gel 416, and placing plunger 420 on diaphragm 418. Fastening retainer 402 to body 404 involves using any suitable rigid attachment structure, for example, retainer 402 may be removably snapped to housing body 404 with hooks in retainer 402 (not shown) and corresponding indentions in housing body 404 (not shown). Alternatively, for example, retainer 402 may be permanently fastened to housing body 404 using an adhesive substance. Retainer 402 and housing body 404 are preferably aligned using any suitable alignment structure, for example, inserting pins (not shown) in retainer 402 into corresponding holes (not shown) in housing body 404. Alternatively, retainer 402 and housing body 404 are, for example, screwed together by providing corresponding threads. Additionally, retainer 402 may be fabricated as an integral feature of housing body 404.

The retainer 402 has a depth of 0.070 inches (1.78 mm) and includes a 0.020 inch (0.508 mm) thick retainer extension 428. Retainer extension 428 is a lip that encircles plunger external interface portion 424 and defines a 0.420 inch (10.7 mm) diameter opening in retainer 402. Retainer relieved region 432 has an inside diameter of 0.490 inches (12.5 mm). Retainer 402 in conjunction with retainer extension 428 captures plunger 420 and retains plunger 420 within force sensor assembly 400 to form an integrated structure. This particular mechanical structure and its attachment methods are illustrative and not limiting, equivalent structures and attachments may also be used.

During operation, retainer 402 not only retains plunger 420, retainer 402 also substantially prevents lateral displacement of plunger 420. When depressed against gel 416 through diaphragm 418, plunger 420 creates force distributions within gel 416. Maintaining a consistent plunger lateral location provides consistent force distributions in gel 416 for a given plunger 420 depression and provides consistent corresponding force measurements. Failure to adequately restrict plunger 420 lateral displacement alters the force distribution in gel 416 which can result in inconsistent force measurements for a given plunger 420 depression.

Referring to FIG. 4, retainer 402 preferably centers plunger 420 on diaphragm 418. A low tolerance between the inside diameter of retainer extension 428 of between 0 and approximately 0.006 inches adequately maintains the lateral disposition of plunger 420.

Integrating plunger 420 into the force sensor assembly 400 advantageously allows calibration of force sensor assembly 400 as a unit prior to incorporating force sensor assembly 400 into a larger system. Calibration of force sensor assembly 400 generally involves applying a known force to plunger external interface portion 424. This force depresses plunger 420 and creates force distributions within gel 416. The resulting data signals from pressure sensor 412 can be compared to the known force and the circuitry on substrate 408 is adjusted accordingly, for example, by laser trimming exposed resistors on substrate 408. The known force may be applied again to verify calibration.

Additionally, the calibrating force is preferably applied to plunger 420 in a manner that generally simulates the expected force distribution within gel 416. For example, a generally symmetric force is applied to plunger 420 to simulate a generally symmetric force distribution representing a centered, impinging I.V. tube on plunger 420.

During operation the actual applied force location may vary from the calibrating force distribution, for example, the plunger 420 may be canted from an asymmetrical force application on plunger 420. A canted plunger 420 could alter force distribution within gel 416 from force distribution resulting from an uncanted plunger 420, and force sensor assembly 412 could provide force information that differs from expected force information.

To provide a force distribution more representative of the calibrating force distribution when operating under variant conditions, various compensating approaches may be used to improve sensor assembly 400 accuracy. For example, a canted plunger 420 can produce a force distribution in gel 416 that generally originates from the more depressed edge. The bottom edges of plunger 420 may be chamfered to compensate for an I.V. tube impingement on plunger 420 that depresses plunger 420 into a canted position. The chamfered edges provide greater plunger 420 surface area contact with diaphragm 418 when canting plunger 420 which creates a force distribution within gel 416 that may more accurately represent the calibrating force sensor assembly 400 force distribution during plunger 420 canted conditions.

When utilized with a solution dispensing system, force sensor assembly 400 preferably does not directly contact the solution and, therefore, need not be periodically disposed for solution contamination reasons.

FIG. 5 illustrates a top view of the force sensor assembly 400. The external dimensions of force sensor assembly 400 may be varied to accommodate connection and mounting features of devices incorporating force sensor assembly 400 such as peristaltic pump and syringe pump housings. The force sensor assembly 400 has an overall length of 0.985 inches (25.53 mm), an overall width of 0.680 inches (17.27 mm), and a depth of 0.280 inches (7.11 mm). Leads 410 have typical lengths of 0.260 inches (10.69 mm), widths of 0.025 inches, and depths of 0.025 inches.

Referring to FIG. 6, a side view of the force sensor assembly 400 is illustrated. Plunger 420 is typically elevated 0.015 inches (0.38 mm) above retainer 402. The plunger 420 exposure depth will vary depending on the expansion and contraction of gel 416 (FIG. 4).

Referring to FIG. 7, a front view of the force sensor assembly 400 is illustrated.

Figure 8:
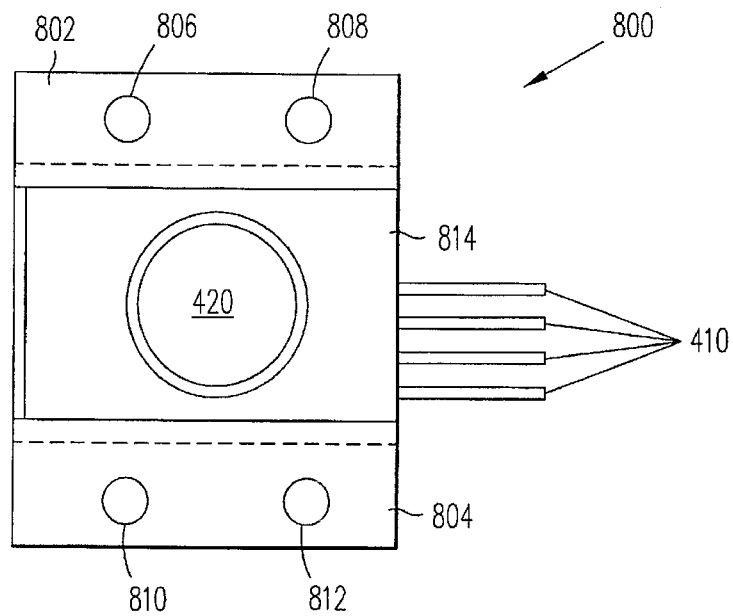
FIG. 8 illustrates a top view of an alternative force sensor assembly embodiment with mounting flanges.
Figure 10:
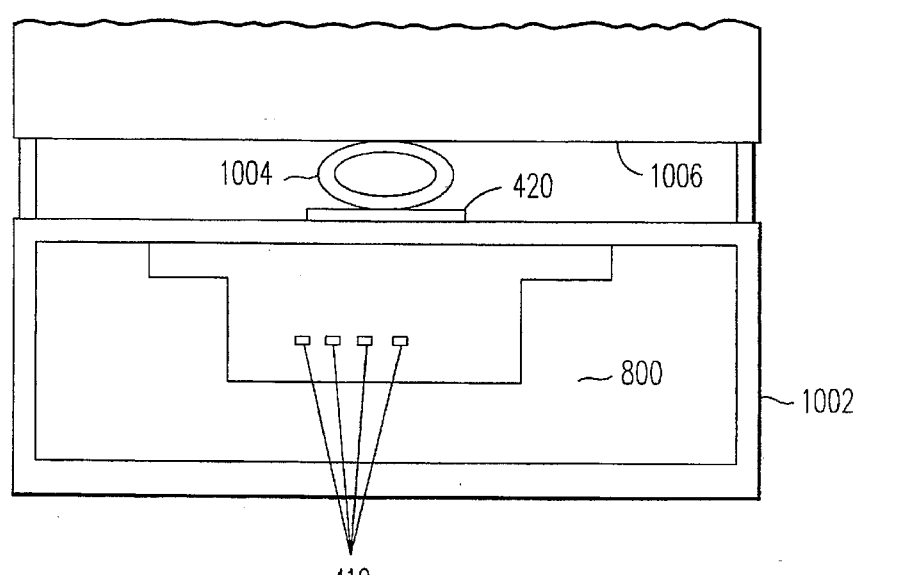
FIG. 10 illustrates a side view of the force sensor assembly of FIG. 8 mounted to a solution dispensing control assembly and engaging a tube.

FIG. 8 illustrates a top view of force sensor assembly 800. FIG. 8 illustrates that a force sensor assembly 800 may vary externally to comply with external considerations, for example, external mounting devices and varying environments, while retaining an integral solid interface. The internal configuration and components of force sensor assembly 800 are identical to those of force sensor assembly 400; however, externally the force sensor assembly 800 configuration differs from force sensor assembly 400. Force sensor assembly 800 includes opposing flanges 802 and 804 for securing force sensor assembly 800 to a pump door 1002 (FIG. 10). Flange 802 includes holes 806 and 808, and flange 804 includes holes 810 and 812 for accommodating fastening devices such as screws or rivets. Additionally, retainer 814 is foreshortened opposite leads 410 corresponding to an opening (not shown) in door 1002 (FIG. 10).

Figure 9:
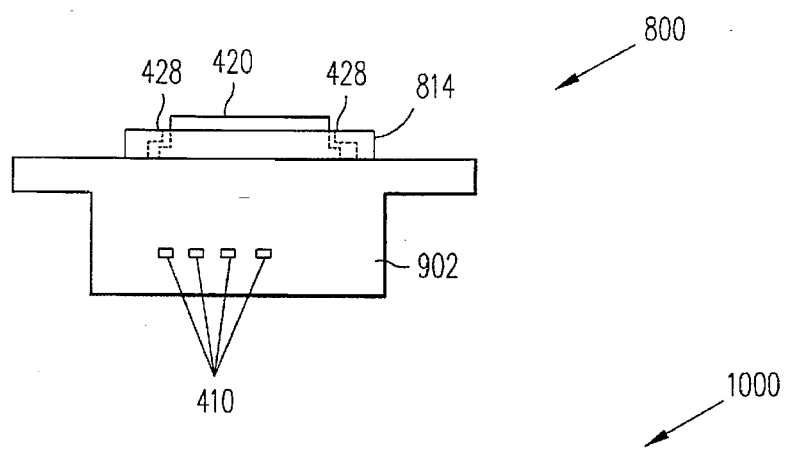
FIG. 9 illustrates a side view of the force sensor assembly of FIG. 8.

FIG. 9 illustrates a side view of force sensor assembly 800 and, in hidden lines, retainer extension 428 which captures plunger 420. Additionally, housing body 902 is attached to retainer 814 in the same manner as the attachment of retainer 402 to housing body 404. Retainer 814 and housing body 902 are also fabricated by injection molding of Ultem® plastic.

FIG. 10 illustrates, in an illustrative application of force sensor assembly 800, a side view of the force sensor assembly 800 mounted to a door 1002 of a solution dispensing control assembly 1000. Plunger 420 extends through an opening in pump door 1002. Leads 410 connect to well-known data acquisition circuitry (not shown). A flexible tube 1004, for example, an I.V. solution tube, extends through the solution dispensing control assembly 1000 and impinges on plunger 420 upon closure of pump door 1002. Tube 1004 is compressed between plunger 420 and rigid surface 1006 and always exerts a force on plunger 420 when pump door 1002 is closed.

The amount of force applied to plunger 420 by tube 1004 corresponds to the compression of tube 1004 and to the pressure of solution within tube 1004. A rise in solution pressure increases the impingement force of tube 1004 on plunger 420, and a solution pressure reduction decreases the impingement force of tube 1004 on plunger 420. Static solution pressure within tube 1004 causes tube 1004 to exert a constant force on plunger 420. The force exerted on plunger 420 causes plunger 420 to exert a force on diaphragm 418 which in turn exerts a force on gel 416. Gel 416 converts the diaphragm 418 force exertion into a pressure exerted on pressure sensor 412. Pressure sensor 412 provides an electronic signal corresponding to the detected force. Amplifier 414 and the integrated circuit network on ceramic substrate 408 provide a conditioned signal to the data acquisition circuitry (not shown).

Figure 11:
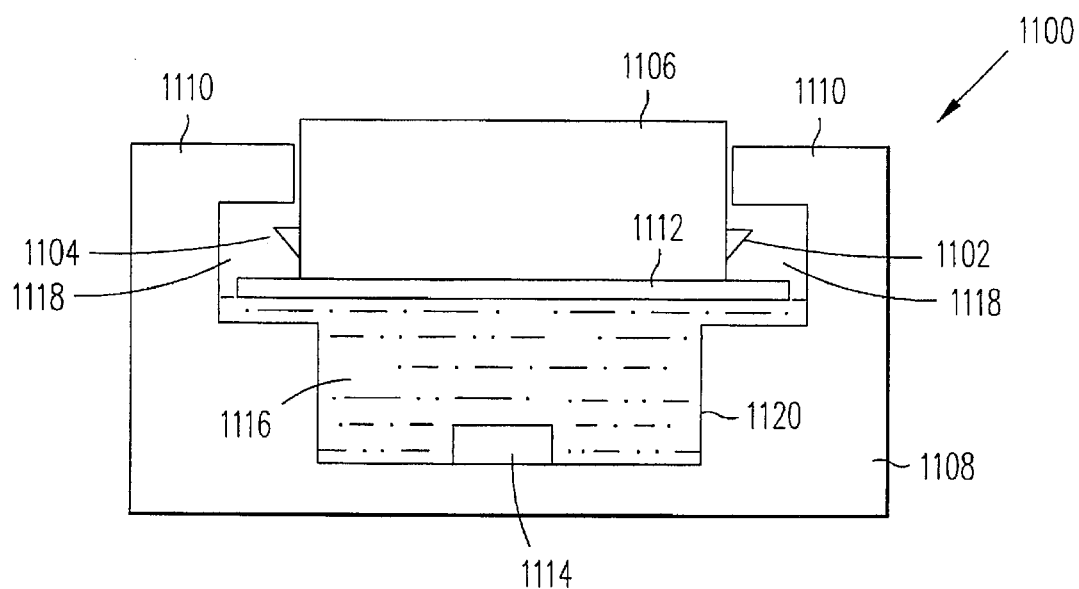
FIG. 11 illustrates a cross-sectional view of a force sensor assembly having flexible tabs for plunger snap insertion into a force sensor housing.

FIG. 11 illustrates a cross-sectional view of force sensor assembly 1100 having moveable tabs 1102 and 1104 that allow housing body 1108, in conjunction with an integral cylindrical retaining lip 1110, to retain plunger 1106. The moveable tabs 1102 and 1104 contract to allow insertion of the lower portion of plunger 1106 into housing 1108 and expand within cavity 1118. The tabs 1102 and 1104 remain substantially rigid when engaging the underside of retaining lip 1110 within cavity 1118 which prevents extraction of plunger 1106 from housing body 1108. The tabs may be of any design which allows retention of plunger 1106 lower portion within housing 1108, for example, the tabs may be a flexible material or a spring loaded mechanism attached to the sidewall of plunger 1106. Additionally, additional tabs may be attached to the sidewall of plunger 1106.

Housing 1108 also includes diaphragm 1112, pressure sensor 1114, and gel 1116. An amplifier and accompanying circuitry (not shown) may be disposed within cavity 1116 and beneath pressure sensor 1114, respectively, substantially as shown in FIG. 4, the amplifier and accompanying circuitry may be coupled externally to the pressure sensor 1114, or the amplifier and accompanying circuitry may utilize a combination of external and internal coupling to the pressure sensor 1114 as will be evident to one of ordinary skill in the art after reading this description. With the exception of tabs 1102 and 1104, the force sensor assembly functions similarly and is made of similar materials as described in conjunction with force sensor assembly 400 (FIG. 4). FIG. 11 also illustrates an alternative gel cavity 1120 configuration.

FIG. 12 illustrates a cross-sectional view of force sensor assembly 1200 having a plunger 1202 disposed within a housing 1204 that directly impinges on gel 1212. Plunger 1202 includes flange 1206 positioned within a retainer cavity 1208. Retainer 1209 may be an integral feature of housing 1204 with, for example, slots to allow passage of a correspondingly slotted flange 1206. A slight rotation of plunger 1202 prevents plunger 1202 escape from housing 1204 when the corresponding slots and flanges are used. Alternatively, retainer 1209 may be a separate device and attached, as discussed in conjunction with retainer 402 (FIG. 4), to housing 1204 subsequent to positioning plunger 1202 in contact with gel 1212.

A close tolerance between the lower portion of plunger 1202 and cavity 1210 sidewalls of approximately less than 0.010 inches (0.254 mm) and preferably as close to 0 inches (0 mm) as possible while allowing lateral plunger 1202 freedom of movement, allows direct contact between plunger 1202 and gel 1212 and prevents gel 1212 leakage. Additionally, higher gel 1212 viscosities allow tolerance reductions between plunger 1212 and cavity 1210 sidewalls while preventing gel 1212 leakage.

Plunger 1202 transmits forces applied to the plunger 1202 top to gel 1212. Pressure sensor 1214 senses the corresponding pressure changes in gel 1212 and transmits pressure information in the form of an electronic output signal to circuitry such as, for example, amplifier 414 (FIG. 4), substrate 408 (FIG. 4), and leads 410 (FIG. 4), which, for example, amplify, filter, and temperature adjust the pressure sensor 1214 output signal. Force sensor assembly 1200 is made of materials similar to those of force sensor assembly 400 (FIG. 4).

While the invention has been described with respect to the embodiments and variations set forth above, these embodiments and variations are illustrative and the invention is not to be considered limited in scope to these embodiments and variations. For example, the plunger may have various geometries that allow retention within a force sensor assembly and provide a solid interface. Accordingly, the plunger retainer may also have various geometries which effectively capture the plunger. Additionally, the retainer extension need not be continuous to effectively capture the plunger. Also, the arrangement of the pressure sensor and amplifier may be varied, for example, the amplifier may be moved outside of the gel cavity. Furthermore, the force sensor assembly may be used to measure both gas and liquid pressures. Additionally, the force sensor assembly geometries, internally and externally, may be varied while continuing to incorporate an integrated solid interface. Moreover, cavity 406 may be filled with liquid, gas, solid materials, or a combination of liquid, gas, or solids to transmit force from the plunger 420 to the pressure sensor 412. When low viscosity liquids or gases are used as pressure transmitters, the pressure sensor housing should be sealed to prevent pressure transmitter leakage. Also, the retainer may include a simple opening without an extension which captures the plunger in the same manner as the retainer extension. All dimensions herein are approximations. Furthermore, the force sensor assemblies of FIG. 4 and following may be made of any suitable materials. Accordingly, various other embodiments and modifications and improvements not described herein may be within the spirit and scope of the present invention, as defined by the following claims.

What is claimed is:

1. A force sensor assembly comprising:
    a housing having a retainer and a cavity, the retainer having an opening in communication with the cavity;
    a pressure sensor at least partially disposed within the housing;
    a rigid interface movably captured by the retainer and having a portion extending through the retainer opening away from the housing, the rigid interface portion extending through the retainer opening having a force receiving surface; and
    a pressure transmitter filling the cavity and in contact with the pressure sensor and coupled to the rigid interface, the rigid interface having translational freedom to exert force, via the pressure transmitter, upon the pressure sensor corresponding to a force received on the force receiving surface of the rigid interface.

2. The force sensor assembly of claim 1 wherein the retainer is removably attached to the housing.

3. The force sensor assembly of claim 1 wherein the retainer opening has a diameter defined by an annular extension, and the rigid interface includes an annular flange disposed within the housing between the extension and the pressure transmitter, the flange having an outside diameter greater than the retainer opening diameter.

4. The force sensor assembly of claim 1 wherein the pressure transmitter includes a gel filling the cavity and in communication with and partially surrounding the pressure sensor, the force sensor assembly further includes:
    a diaphragm interposed between the solid interface and the gel having a first surface in communication with the gel and a second opposing surface in contact with the rigid interface.

5. The force sensor assembly of claim 4 wherein the gel is a silicone based gel and the diaphragm is a fabric reinforced elastomer membrane.

6. The force sensor assembly of claim 4 wherein the diaphragm is free-floating.

7. The force sensor assembly of claim 1 further comprising:
    an amplifier disposed within the cavity and electrically coupled to the pressure sensor.

8. The force sensor assembly of claim 1 wherein the housing includes a bottom surface comprised of a ceramic substrate, the ceramic substrate having a resistor network and a plurality of leads formed thereon, wherein the pressure sensor is mounted on the ceramic substrate.

9. The force sensor assembly of claim 1 wherein the retainer is removably attached to the housing.

10. The force sensor assembly of claim 1 wherein the pressure sensor is a micro-machined silicon pressure sensor.

11. The force sensor assembly of claim 1 wherein the rigid interface is a generally cylindrical plastic plunger.

12. The force sensor assembly of claim 1 wherein the housing is comprised of a rigid plastic.

13. A force sensor assembly for sensing externally applied force comprising:
    a housing body having a first surface, a second surface, a first compartment, a second compartment in communication with the first compartment, and a third compartment in communication with the second compartment;

a platform coupled to the housing body first surface;

a pressure sensor disposed on the platform and in communication with the housing body third compartment;

a retainer body, coupled to the housing body second surface, and having an orifice opening to the housing body third compartment;

a pressure transmission material disposed in at least the second and third housing body compartments;

a diaphragm, disposed in the housing body first compartment, having a first surface in communication with the pressure transmission material and having a second surface opposite the first surface; and a solid, rigid interface disposed through the retainer body orifice, the solid interface being movably captured by the retainer body, wherein the retainer body substantially restricts lateral displacement of the solid interface and permits captured, longitudinal movement, and the solid, rigid interface having a first surface to receive the externally applied force and a second surface in contact with the diaphragm second surface to exert force, corresponding to the externally applied force, through the diaphragm and the pressure transmission material to the pressure sensor.

14. The force sensor assembly as in claim 13 wherein the first compartment is cylindrical, the second compartment is a conical section tapering away from the first compartment and having a base diameter, the third compartment is a rectangular volume, and the first compartment has a diameter greater than the second compartment base diameter.

15. The force sensor assembly as in claim 13 wherein the diaphragm is free-floating.

16. The force sensor assembly as in claim 13 wherein the platform is a ceramic substrate having an integrated resistor network formed thereon.

17. The force sensor assembly as in claim 13 wherein the solid interface is a plunger having three cylindrical sections, and the retainer orifice is annular;

wherein the plunger first section has a diameter less than a diameter of the retainer orifice, is disposed within the orifice, and extends beyond the orifice away from the housing body;

wherein the plunger second section has a diameter greater than the retainer orifice diameter;

wherein the plunger third section has the surface in contact with the diaphragm; and wherein the retainer orifice and the plunger are generally axially aligned.

18. The force sensor assembly as in claim 13 wherein the retainer orifice is defined by an annular continuous lip to longitudinally capture the solid interface.

19. The force sensor assembly as in claim 13 wherein the diaphragm is a cylindrical interface elastomer membrane.

20. The force sensor assembly as in claim 13 wherein the pressure transmission compound is a silicone based gel.

21. The force sensor assembly as in claim 13 wherein the pressure sensor is at least partially disposed in the housing body first compartment.

22. A method comprising the steps of:

retaining at least a portion of a rigid interface within a housing to substantially prevent lateral displacement of the rigid interface while allowing captured, longitudinal movement of the rigid interface;

applying a force to the rigid interface to translate the rigid interface;

generating a generally symmetric force distribution within a pressure transmission medium filling a chamber within the housing, wherein the generally symmetric force distribution corresponds to the force applied to the rigid interface;

transmitting a force corresponding to the force applied to the rigid interface, via the pressure transmission medium, to a pressure sensor disposed within the housing; and providing an output from the pressure sensor corresponding to the applied force.

23. The force sensor assembly of claim 1 wherein the retainer substantially prevents lateral displacement of the rigid interface.

24. The force sensor assembly of claim 1 wherein the rigid interface is a plunger having chamfered edges to compensate for a nonuniform force application upon the plunger.

25. The force sensor assembly of claim 1 further comprising:

a solution dispensing control assembly having a flexible tube that impinges upon the rigid interface, wherein the flexible tube is capable of applying the force, corresponding to a pressure of a solution in the tube, which is received on the force receiving surface of the rigid interface.

26. The method of claim 22 further comprising the step of:

compensating for a nonsymmetrical force application in the force applying step.

27. The method as in claim 26 wherein the step of compensating further comprises the step of:

maintaining a generally consistent surface area contact of the rigid interface upon pressure transmission medium.

28. The method of claim 22 wherein the pressure transmission medium includes silicone based gel, and the step of transmitting comprises the step of:

distributing the applied force in the silicone based gel;

the method further comprising the step of:

sensing the applied force distributions in the silicone based gel with the pressure sensor.

29. The method of claim 22 wherein the step of transmitting comprises the step of:

transmitting the force applied to the rigid interface to the pressure transmission medium via a diaphragm disposed on a surface of the transmission medium.

30. A force sensor assembly for measuring a force applied through a flexible wall, the force sensor assembly comprising:

a housing having a cavity and a retainer;

a housing having a cavity and a retainer;

a pressure transmission solution filling the cavity;

a rigid interface captured by the retainer and having substantially restricted lateral freedom of movement, the interface having a rigid first surface to receive the force applied through the flexible wall, the interface further having a rigid second surface to provide a generally symmetric force distribution within the pressure transmission solution corresponding to the applied force; and a pressure sensor in contact with the pressure transmission solution.

31. The force sensor assembly as in claim 30 wherein rigid interface includes chamfered edges to compensate for an asymmetrical application of force applied through the flexible wall.

32. The force sensor assembly as in claim 30 wherein the cavity includes a conical section tapering away from the rigid interface.

33. The force sensor assembly as in claim 30 further comprising:

a solution dispensing assembly having a tube impinging upon the rigid interface, wherein the tube includes the flexible wall.

* * * * *